(12) United States Patent
Waters, Sr. et al.

(10) Patent No.: US 6,595,939 B2
(45) Date of Patent: *Jul. 22, 2003

(54) DISPOSABLE CLEANING APPARATUS FOR HUMAN BODY PART

(76) Inventors: Joe C. Waters, Sr., 4047 Mullikin Rd., Evans, GA (US) 30809; June M. Abernathy, 4515 Saks Rd., Anniston, AL (US) 36206

( * ) Notice: Subject to any disclaimer, the term of this patent is extended or adjusted under 35 U.S.C. 154(b) by 0 days.

This patent is subject to a terminal disclaimer.

(21) Appl. No.: 10/037,887

(22) Filed: Jan. 10, 2002

(65) Prior Publication Data

US 2002/0077607 A1 Jun. 20, 2002

Related U.S. Application Data

(63) Continuation-in-part of application No. 09/375,491, filed on Aug. 17, 1999, now Pat. No. 6,358,221.

(51) Int. Cl.[7] .................................................. A61F 9/00
(52) U.S. Cl. ........................................ 604/1; 606/162
(58) Field of Search .......................... 604/1–3; 606/162, 606/188

(56) References Cited

U.S. PATENT DOCUMENTS

| 3,203,418 | A | * | 6/1962 | Johnston |
| 3,500,829 | A | * | 3/1970 | Abramowitz |
| 4,497,402 | A | * | 2/1985 | Karos |
| 4,798,216 | A | * | 1/1989 | McCarty et al. |
| 5,183,461 | A | * | 2/1993 | Hobbs |
| 5,931,845 | A | * | 8/1999 | Amyette |
| 6,146,398 | A | * | 11/2000 | Satterfield |
| 6,358,221 | B1 | * | 3/2002 | Waters et al. |

* cited by examiner

*Primary Examiner*—Dennis Ruhl

(57) ABSTRACT

A disposable kit for achieving and maintaining clean and healthy tissue in body piercing sites on the human body including the eyebrow, chin, nose, mouth, tongue, navel, nipples, and private parts, by cleaning, sterilizing and applying an antiseptic and antibacterial solution. Prevents body piercing complications most often related to the absence of a suitable sterile environment, e.g., using piercing tools or instruments that are not sterile, or the insertion of non-sterile or contaminated appliances, rings, hooks, or whatever device or product is inserted into the pierced cavity. Designed to prevent problems such as irritation, soreness, and closure of the desired pierced opening, which results from contamination, and the absence of a proper sterile and aseptic cleaning kit.

12 Claims, 2 Drawing Sheets

DISPOSABLE CLEANING APPARATUS FOR HUMAN BODY PART

This application is a continuation-in-part of application Ser. No. 09/375,491 filed Aug. 17, 1999, now U.S. Pat. No. 6,358,221.

BACKGROUND OF THE INVENTION

An improvement has been made to our original application (Ser. No. 09/375,491) to make the disposable cleaning apparatus for pierced human body parts more user friendly. The new design eliminates the need to manually thread the textured cleaning string for each use. Additionally, we have introduced new packaging for the new "C" shaped insertion tools and textured cleaning strings. The packaging, moisture proof foil or plastic envelopes, contains antiseptic solution or antibacterial solution. In addition to the antiseptic solutions alcohol, iodine, boric acid, we have added another antiseptic solution, which is oil extracted from the leaves of *Malaleuca alternifolia* trees.

BRIEF SUMMARY OF THE INVENTION

An improvement has been made to U.S. Pat. No. 6,358,221 with a minor modification to the "C" shaped insertion tool and its associated packaging. Our newer model "C" shaped insertion tool keeps the same design on the round end as shown in U.S. Pat. No. 6,358,221; however, the threading eye has been redesigned with a sleeved or hollowed end into which the textured cleaning string is fitted and crimped. This makes the insertion tool more user friendly and eliminates the need to thread the string into the insertion tool. There are no known "C" shaped insertion tools with sleeved or hollowed ends for crimping textured cleaning strings for disposable body piercing cleaning kits used for the routine care of these inner sites of the human body.

The insertion tools come fully assembled (threaded) and are pre-soaked in either antiseptic or antibacterial solution. The contents are sealed in moisture proof foil or plastic envelopes for convenient use. Pre-packaged alcohol prep pads are utilized for cleaning and sterilizing the pierced body site before each use of this cleaning apparatus.

We also believe that it is significant that we are the first to use oil extracted from the leaves of *Malaleuca alternifolia* trees as an antiseptic for cleaning pierced body sites.

DETAILED DESCRIPTION OF THE INVENTION

Figure 1:
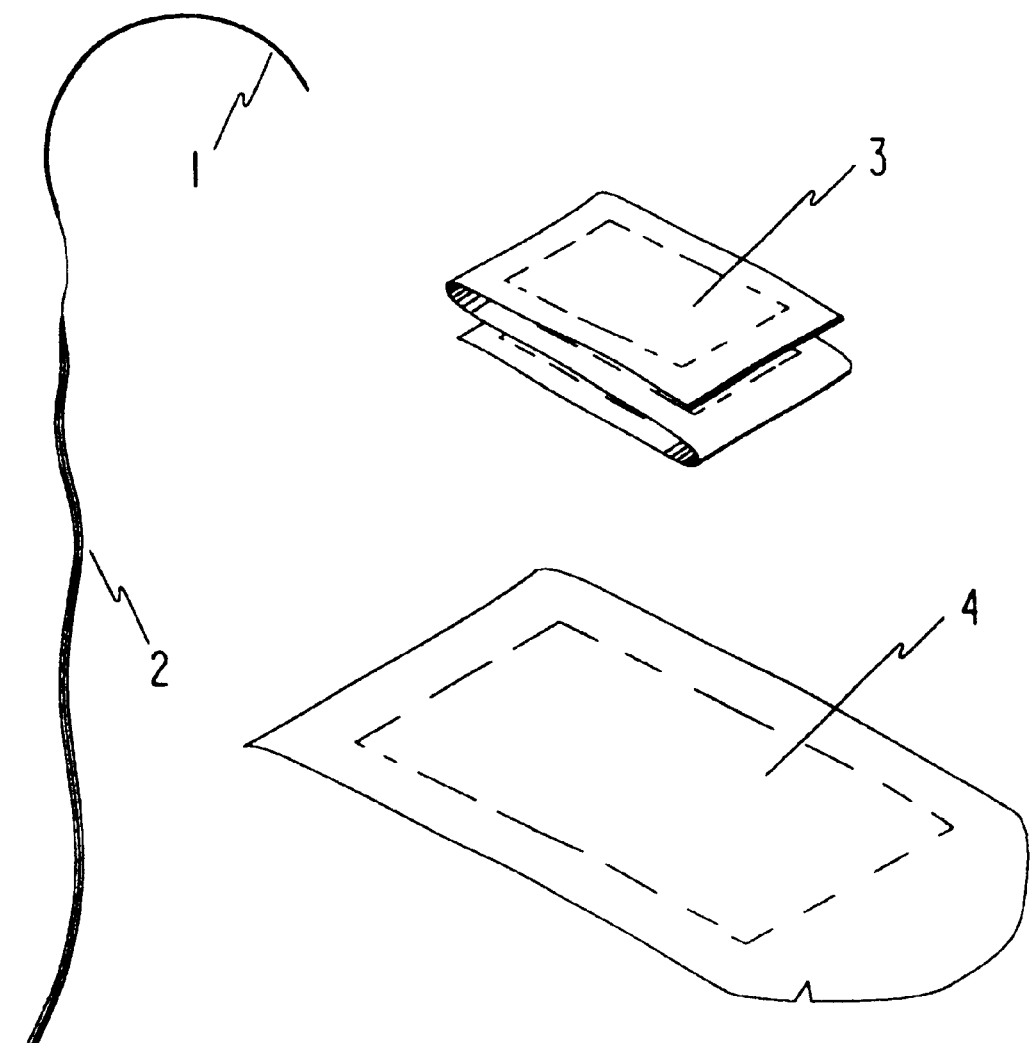
FIG. 1 shows a complete "Disposable Cleaning Apparatus for Human Body Parts". The "C" shaped insertion tool 1 with thread 2 is prepackaged in a sealed foil or plastic packaging envelope 3 and a prepackaged alcohol swab 4 is provided for cleaning and disinfecting the pierced body site.

The basic materials utilized in this invention, with all being shown in FIG. 1, include: a "C" shaped insertion tool 1 with thread 2, which is prepackaged in a sealed foil or plastic packaging envelope containing antiseptic solution or antibacterial solution 3, a prepackaged alcohol swab 4 for cleaning and disinfecting the pierced body site.

Figure 2:
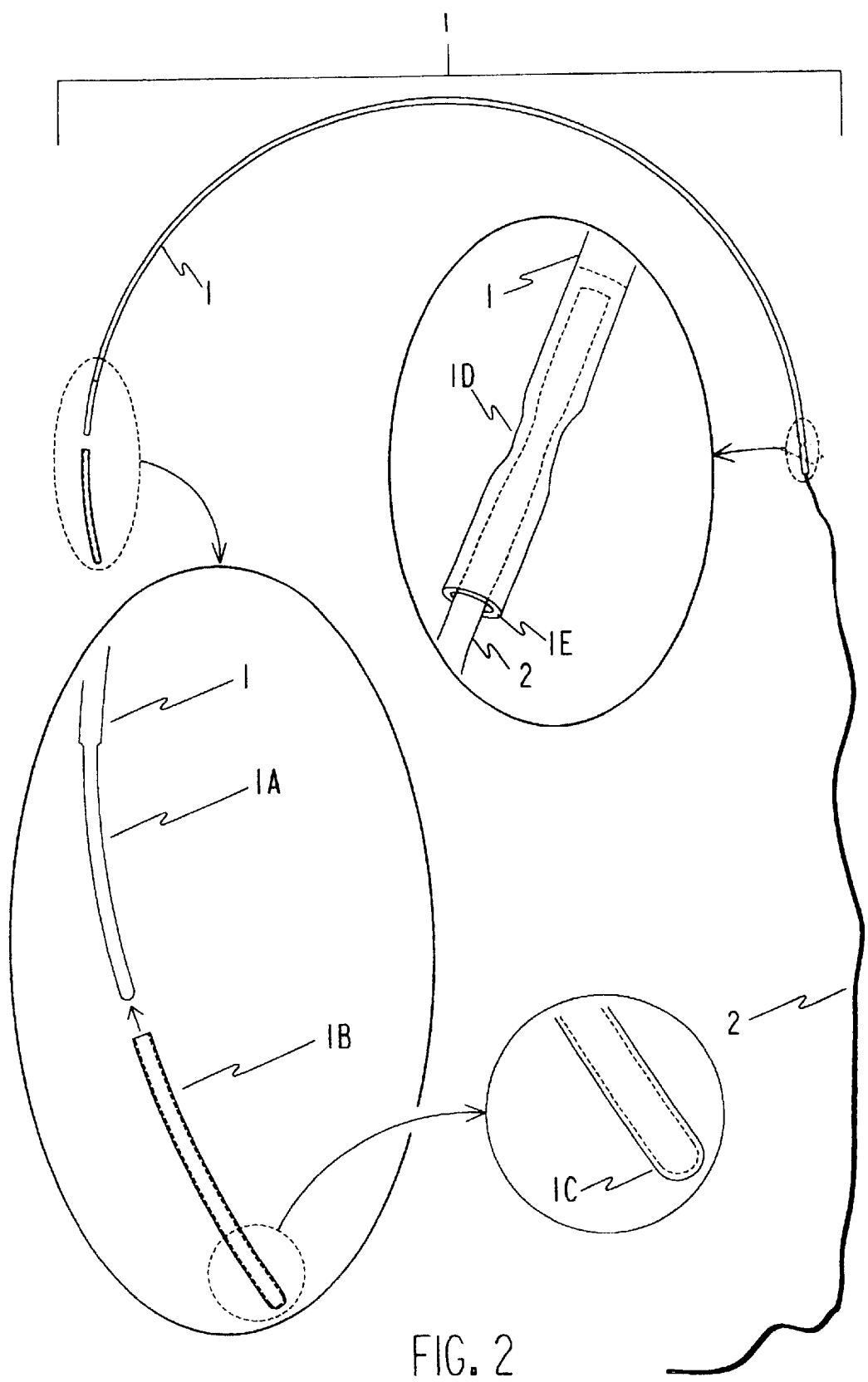
FIG. 2 is a detail view of the "C" shaped insertion tool 1 with a cleaning string attached 2. The cleaning string 2 is shown having been inserted into the sleeved or hollowed end 1E of the insertion tool being held in place by a crimped section ID of the insertion tool.

FIG. 2, Shows the "C" shaped insertion tool 1 has been modified to include a sleeved or hollowed end 1E wherein the cleaning string 2 is inserted into the sleeve or hollowed end 1E and crimped 1D. This eliminates the necessity for manual threading. The textured cleaning strings are made of cotton, polyester, or nylon.

The term "antiseptic solution" as used herein is defined to include, but not be limited to alcohol, iodine, boric acid, and oil extracted from the leaves of *Malaleuca alternifolia* trees, an oil found in the Northeast region of New South Wales, Australia. This oil has significant antiseptic properties and is considered an ideal skin disinfectant against a range of organism and is non-irritating to the skin.

The term "antibacterial solution" as used herein is defined to include, but not be limited to commercially available mouthwash with antibacterial properties.

FIG. 1 is a perspective view showing a second embodiment of a disposable cleaning apparatus for pierced human body parts which includes an insertion tool 1 with a textured string attached 2 and sealed moisture-proof envelope packages made of aluminum foil or plastic or other material 3 containing the insertion tool and antiseptic or antibacterial solution and the same type envelope 4 containing alcohol swabs for cleaning the pierced body site.

FIG. 2 is a detailed view showing a second embodiment of an insertion tool with one end 1A and 1B being the same insertion tool as described in the original application with the only difference being the other end 1D and 1E has a sleeved or hollowed crimped end with a textured string 2 being permanently attached.

What is claimed is:

1. A disposable body piercing cleaning kit for cleaning inside human body piercing sites which comprises:
   a plurality of "C" shaped insertion tools;
   textured cleaning strings;
   cleaning and disinfecting alcohol prep pads;
   sealed moisture proofed envelopes with antiseptic solution; and
   sealed moisture proofed envelopes with antibacterial solution.

2. A cleaning kit as in claim 1, wherein said insertion tools are "C" shaped and have one end comprising a round end.

3. A cleaning kit as defined in claim 2, wherein the round end of said "C" shaped insertion tools are covered by a plastic material.

4. A cleaning kit as defined in claim 1, wherein said "C" shaped insertion tools have one end sleeved or hollowed.

5. A cleaning kit as defined in claim 4, wherein said "C" shaped insertion tools have a textured cleaning string crimped in the sleeved or hollowed end.

6. A cleaning kit as defined in claim 1, wherein the "C" shaped insertion tools, and textured cleaning strings are packaged in sealed moisture proofed envelopes containing antiseptic solution.

7. A cleaning kit as defined in claim 1, wherein the "C" shaped insertion tools, and textured cleaning strings are packaged in sealed moisture proofed envelopes containing antibacterial solution.

8. A cleaning kit as defined in claim 1, wherein said antibacterial solution comprises a mouthwash solution, which has antibacterial properties.

9. A cleaning kit as defined in claim 1, wherein said antiseptic solution is oil extracted from the leaves of *Malaleuca Altemifolia* trees.

10. A cleaning kit as defined in claim 1, wherein said textured cleaning strings are made of cotton.

11. A cleaning kit as defined in claim 1, wherein said textured cleaning strings are made of polyester.

12. A cleaning kit is defined in claim 1, wherein said textured cleaning strings are made of nylon.

* * * * *